United States Patent [19]

Peterson et al.

[11] 4,378,807
[45] Apr. 5, 1983

[54] BLOOD PRESSURE MEASUREMENT APPARATUS

[75] Inventors: Ronald T. Peterson; Israel M. Stein, both of Brookline, Mass.

[73] Assignee: Clinical Data, Inc., Brookline, Mass.

[21] Appl. No.: 212,764

[22] Filed: Dec. 3, 1980

[51] Int. Cl.³ ............................................. A61B 5/02
[52] U.S. Cl. .................................. 128/677; 128/680; 128/682; 128/900
[58] Field of Search ............... 128/672, 677, 680–682, 128/687–689, 773, 900, 683, 691, 694

[56] References Cited

U.S. PATENT DOCUMENTS

| | | | |
|---|---|---|---|
| 2,039,000 | 4/1936 | Hesse | 128/681 |
| 2,571,124 | 10/1951 | Farrand | 128/680 |
| 2,821,188 | 1/1958 | Pigeon | 128/683 |
| 2,827,040 | 3/1958 | Gilford | 128/681 |
| 3,104,661 | 9/1963 | Halpern | 128/683 |
| 3,156,237 | 11/1964 | Edmark, Jr. | 128/683 |
| 3,236,230 | 2/1966 | Follett | 128/683 |
| 3,452,744 | 7/1969 | Van Den Nieuwenhof et al. | 128/683 |
| 3,508,537 | 4/1970 | Kahn et al. | 128/683 |
| 3,527,204 | 9/1970 | Lem et al. | 128/686 X |
| 3,552,383 | 1/1971 | Krueger et al. | 128/682 |
| 3,654,915 | 4/1972 | Sanctuary | 128/682 |
| 3,712,297 | 1/1973 | Greene, Jr. et al. | 128/204 X |
| 3,730,172 | 5/1973 | Buddecke et al. | 128/682 |
| 3,905,353 | 9/1975 | Lichowsky | 128/677 |
| 3,918,436 | 11/1975 | Peart et al. | 128/677 |
| 4,050,452 | 9/1977 | Lee | 128/683 |
| 4,058,117 | 11/1977 | Kaspari et al. | 128/682 |
| 4,112,929 | 9/1978 | Affeldt et al. | 128/680 |
| 4,116,230 | 9/1978 | Gorelick | 128/680 |
| 4,167,181 | 9/1979 | Lee | 128/682 |
| 4,216,779 | 8/1980 | Squires et al. | 128/682 |
| 4,252,127 | 2/1981 | Gemelke | 128/683 X |
| 4,262,675 | 4/1981 | Kubo et al. | 128/680 |
| 4,328,810 | 5/1982 | Hill et al. | 128/680 |

FOREIGN PATENT DOCUMENTS

| | | | |
|---|---|---|---|
| 14720 | 9/1980 | European Pat. Off. | |
| 2466975 | 4/1981 | France | 128/680 |

OTHER PUBLICATIONS

Schneider, *Journal of Applied Physiology*, 37, 5, 776, (1974).

*Primary Examiner*—Lee S. Cohen
*Assistant Examiner*—Angela D. Sykes
*Attorney, Agent, or Firm*—Martin LuKacher

[57] ABSTRACT

Long-term blood pressure measuring apparatus, particularly adapted for ambulatory blood pressure monitoring where the subject can be engaged in normal activities while blood pressure is being measured and to be worn by the subject whose blood pressure is to be measured uses an inflatable cuff, a pump for inflating the cuff, valves for controlling the pressure in the cuff, sensors for the cuff pressure and for auscultatory (Korotkoff) sounds from the subject, a recorder for recording the sounds and blood pressure measurement cycle control circuits. The control circuits provide for blood pressure measurement cycles to recur repetitively at predetermined time intervals, for example every 30 or 60 minutes over a period of many hours, as well as when the subject manually activates the cycle control circuit to produce a blood pressure measurement cycle, but only when an automatic cycle occurs between successive manual cycles so as to limit the frequency of the blood pressure measurement so as to prevent harm to the subject and to conserve power needed for long-term operation of the apparatus. Circuits which control a valve use a linear ramp generator and triangular wave generator to provide a linear change in cuff pressure while the auscultatory sounds are recorded to enable accuracy of indication of the blood pressure from the recorded sounds.

21 Claims, 3 Drawing Figures

BLOOD PRESSURE MEASUREMENT APPARATUS

DESCRIPTION

The present invention relates to blood pressure measurement apparatus and particularly to apparatus for making a number of successive blood pressure measurements over a long period of time automatically or when such measurements are called for by the subject or patient whose blood pressure is being measured.

The invention is especially suitable for use in providing long-term ambulatory blood pressure measurement in apparatus which is portable and can be worn by the subject for many hours, say 12 or 24 hours, during the patient's normal activities and recording the auscultatory (Korotkoff) sounds obtained from a sensor which is coupled to an appendage, such as the arm, of the subject which is constricted by an inflatable cuff on the subject's arm.

The need for long-term measurement of blood pressure levels has been recognized, and portable apparatus has been proposed for the purpose of long-term ambulatory blood pressure measurement (see Schneider, Kimmell, and Meter, *Journal of Applied Physiology*, 37, 5, 776 (1974) and U.S. Pat. No. 4,216,779 issued Aug. 12, 1980 and U.S. Pat. No. 3,712,297.) The need still exists for long-term blood pressure measuring apparatus which provides accurate blood pressure data from the auscultatory sounds accompanying the constriction of the patient's arm. The problem of providing accurate data is complicated by the need to maintain portability and long-term operation of the apparatus, for example about 80 measurements without attention to the apparatus. Another need is to provide for measurements automatically at certain intervals, for example every 30 minutes, as well as when the patient is concerned with his or her condition, for example under stressful situations. The blood pressure measurement involves the constriction of the arm and the artery. Too many cuff inflations can be harmful. Each inflation draws power from the portable power source, for example a battery, and can prevent long-term operation. The measurement data from closely successive manually activated measurements is not advantageous in that it may not provide additional significant medical information, and much inconvenience and potential harm may result to the subject.

Accordingly, it is an object of the present invention to provide improved blood pressure measurement apparatus.

It is another object of the invention to provide improved apparatus for a long-term measurement of blood pressure which makes a large number of blood pressure measurements over a long period of time, such as over a 12 or 24 hour period.

It is a further object of the present invention to provide improved apparatus for monitoring the blood pressure of the subject over a long period of time and which may be portable and worn by the subject and used to record the blood pressure measurements which are made during measurement cycles which recur automatically or when activated by the patient while the patient engages his or her normal daily activity.

It is a still further object of the present invention to provide improved long-term blood pressure measurement apparatus which senses and may record and indicate data which accurately reflect the blood pressure of the subject during each of many measurements which may occur over the long term.

It is a still further object of the present invention to provide improved long-term blood pressure measurement apparatus which may be activated automatically at predetermined intervals of time or manually by the subject, but with a frequency which reduces the possibility of harm to the subject and conserves power so as to adapt the apparatus for portable operation.

Briefly described, blood pressure measuring apparatus embodying the invention uses an inflatable cuff which constricts an appendage of a subject whose blood pressure is to be measured. Means such as the pump is provided for changing the pressure in the cuff, for example inflating the cuff and then stopping so as to permit a valve associated with the cuff to deflate the cuff. Means, such as a microphone held by the cuff on the appendage, senses the auscultatory sounds from the appendage while the pressure in the cuff is changing. It is preferable to utilize the change in pressure upon deflation of the cuff in order to reduce the effect of noise produced by the pump while inflating the cuff. A recorder may be used to record the auscultatory sounds. The pressure in the cuff is also monitored and a signal having an amplitude which corresponds to the cuff pressure is generated. Means for controlling the valve are operative to linearize the change in pressure in the cuff while the auscultatory sounds are being produced and recorded. A reference linear ramp signal generator, a source of triangular waves which repeat at a high rate (such that many occur during the period of the ramp signal), and circuits for comparing the ramp signal with the signal representing the pressure in the cuff to produce an output which is compared with the triangular wave result in pulses having a width which varies with the deviation from the linear ramp of the pressure signal from the cuff. These pulses are applied to the valve so as to control the cuff pressure and provide a linear pressure change. The auscultatory sounds therefore occur along a linear time base and indicate accurately the subject's blood pressure.

The apparatus also includes means for controlling each blood pressure measurement cycle in response to commands for the initiation of each cycle. A command may be produced automatically at predetermined intervals, so as to initiate automatic measurement cycles, or by the subject, manually. The measurement cycle control means has means for controlling the frequency of the manually activated cycle. When a manual cycle is initiated, information as to the occurrence of the manual cycle is stored and used to inhibit subsequent manual cycles unless there is an automatic cycle between successive manual cycles. Also the measurement cycle control means is operative to prevent a measurement cycle from being manually activated while a blood pressure measurement cycle is in progress.

The foregoing and other objects, features and advantages of the invention as well as the presently preferred embodiment thereof will become more apparent from a reading of the following description in connection with the accompanying drawing in which.

Figure 1:
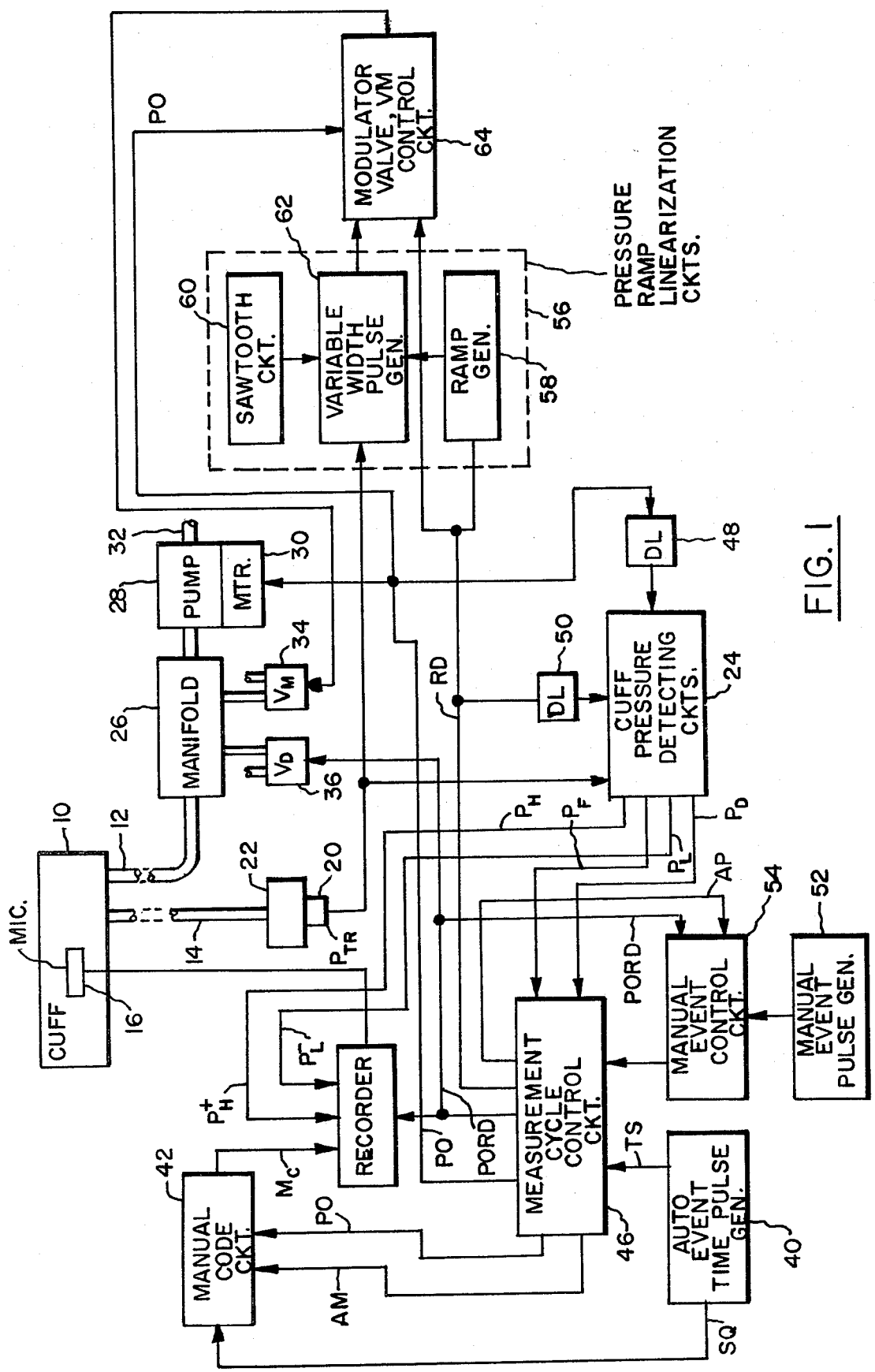
FIG. 1 is a block diagram of blood pressure measurement apparatus in accordance with the invention which is adopted for the long-term recording of blood pressure data by being worn or carried by the subject whose blood pressure is being measured.

Referring first to FIG. 1 there is shown a cuff 10 having a bladder to which connections are made by two tubes 12 and 14. The cuff is adapted to be wrapped around an appendage, such as the arm, of the subject, such as the patient, whose blood pressure is to be measured at intervals over a long period of time of several hours, say from 6 to 24 hours. The cuff is designed from thin walled material which will not withstand sustained pressure which might harm the patient due to arm constriction (e.g. 300 mm Hg.). There is a safety feature of the apparatus in that the tubes 12 & 14 are desirably connected to the apparatus via a quick disconnect coupling which immediately drops the cuff pressure, thereby avoiding potential harm in case of excessive pressures & cuff constriction. The blood pressure measurements are made by sensing the auscultatory or Korotkoff sounds issued by the artery of the patient as it is constricted by the cuff or while the constriction is released. A sensor which may be a crystal microphone 16 is held to the arm by the cuff and detects the auscultatory sounds. Also detected are the vibrations coupled to the arm as the cuff is inflated. The inflation vibrations may be used as a marker to indicate the beginning of a blood pressure masurement cycle. A pressure transducer 20, which may be a body of PZT or a strain gauge element coupled to a diaphragm is connected via the tube 14 to the cuff to sense the cuff pressure. The transducer 20 is indicated in the drawing as $P_{TR}$ and is located in the lower part of a small manifold 22 which distributes the pressure over the diaphragm of the transducer 20. A signal having an amplitude corresponding to the pressure in the cuff 10 is produced by the transducer 20 and applied to cuff pressure detecting circuits 24.

The tube 12, which may be a flexible, somewhat elongated tube, for adding compliance to damp or isolate vibrations generated during inflation and deflation of the cuff, is connected to a manifold 26. A pump 28, which may be a diaphragm pump driven by a brushless, low noise motor 30 and vented on the return side thereof by a tube 32 to the atmosphere, is connected to the manifold 36. Also connected to the manifold are two solenoid operated valves 34 and 36. The valve 34 indicated as $V_M$, is a modulating valve. The opening and closing of this valve 34 modulates the pressure in the cuff in the course of the deflate portion of the cycle, during the sensing of the auscultatory sounds and the recording thereof by a recorder 38, which may be a miniature magnetic tape cassette recorder. The other valve 36 is indicated in the drawing as a $V_D$, and is operated as a dump valve to open the manifold to the atmosphere and dump or maintain the pressure in the cuff 10 at atmospheric pressure between measurement cycles.

It is preferred to use the modulating valve 34 to control and linearize the change in pressure of the cuff to a linearly decreasing pressure during the deflation portion of the cycle, while the constriction is released and when the auscultatory sounds are detected and recorded. It will be appreciated that the inflation cycle may also be used, in which case the ramp is linearized by modulating the cuff pressure as the pump inflates the cuff. Inasmuch as vibrations are generated during "pump-up" or inflation of the cuff which may mask the auscultatory sounds or be considered as artifacts (erroneous auscultatory sounds), the deflation portion of the cycle is used in accordance with this preferred embodiment of the invention. The pressure transducer 20 may also be used to detect the auscultatory sounds. Inasmuch as the microphone 16 is more sensitive and is more closely coupled to the arm of the subject, a microphone is used in the preferred embodiment of the invention which is illustrated herein.

The recorder 38 has an amplifier for the auscultatroy sound signals 16 from the microphone. This amplifier may also have inputs for signals indicating that the pump is inflated to predetermined pressures. These may be a predetermined high pressure $P_H$ and a predetermined low pressure $P_L$. The high pressure may for example be somewhat above a systolic pressure. The low pressure $P_L$ may be just below a diastolic pressure. For example $P_H$ may be 160 millimeters (mm) of mercury (Hg) and $P_L$ may be 40 mm of Hg. Signals corresponding to $P_H$ and $P_L$ are preferably generated by the cuff pressure detecting circuits as pulses of opposite polarity, as by the use of oppositely polarized inputs of different comparators to generate the pulses or as a step waveform with a step down and a step up to indicate the $P_H$ and $P_L$ points.

Another input to the input signal amplifier of the recorder 38 is a manual code, MC, signal. This signal may be a square wave or pulse train obtained from the divider circuits in the automatic event time pulse generator 40 which generates commands TS to automatically initiate a measurement cycle at preselected time intervals. TS commands may occur selectively once an hour, twice an hour, four times an hour or even eight times an hour (i.e., every 60, 30, 15 or 7.5 minutes), as the physician desiring the blood pressure information may prescribe. To this end, the automatic event time pulse generator may include a clock oscillator and a chain of dividers for producing the TS signals at the selected time intervals. This divider outputs a pulse train SQ to a manual code circuit 42. This circuit is shown in greater detail in FIG. 2. Manual events are activated by a manual event pulse generator 52 which includes a switch 44 which is adapted to be operated by the subject. When the switch is operated, the SQ signal is recorded as a manual code, MC, by the recorder 38, so long as a manual blood pressure measurement cycle is allowed as indicated by inputs to the manual code circuit 42, AM and $\overline{PO}$ which are produced by a measurement cycle control circuit 46.

The cuff pressure detecting circuits 24 include reference voltages which are calibrated to correspond to certain cuff pressures as indicated by the amplitude of the output signals from the pressure transducer 20. The pressure transducer signal and a pressure voltage corresponding to the high pressure $P_H$ (e.g., 160 mm of Hg) is applied to a comparator to produce the $P_H$ output pulse or step which goes to the recorder 38. Another comparator, oppositely polarized, compares another voltage corresponding to $P_L$ (e.g., 40 mm of Hg) and provides the $P_L$ output pulse or step of polarity opposite the the $P_H$ pulse to the recorder 38. An output $P_F$ indicating that the pump has inflated to a predetermined high pressure above the expected systolic pressure (for example selectively 200 mm or 240 mm of Hg) is provided by still another comparator in the cuff pressure detecting circuit 24. This other comparator may have its output connected to a gate to which an input from the measurement cycle control circuits 46 indicating the start of a measurement cycle, PO, is connected via a delay circuit 48. The input PO indicates that the pump is on, in that the leading edge of this signal PO corresponds to the initiation of the measurement cycle. A RC circuit contained in the delay circuit 48 may be permitted to charge. The time constant of this RC circuit may for example be 20 seconds. After 20 seconds a signal is generated by the delay circuit. Accordingly, 20 seconds after the start of the measurement cycle a $P_F$ output from the cuff pressure detecting circuits is generated in any event. The $P_F$ signal indicates that the pump is or should be finished inflating the cuff.

Another comparator in the cuff pressure detecting circuits 24 compares a reference voltage corresponding to a low cuff pressure, for example 35 mm of Hg, and provides an output upon occurrence thereof. This output may be connected to a gate which alternatively generates the $P_D$ output a predetermined time after the deflation portion of the cycle has commenced. This is indicated by a level RD from the measurement cycle control circuits 46 which has a leading edge concurrent with the beginning of the deflation of the cuff. A delay circuit 50, with a RC timing circuit similar to that in the other delay circuit 48, produces an output a predetermined time after the beginning of the deflation cycle (after the leading edge of the RD level). Accordingly, a $P_D$ output will be applied to the measurement cycle control circuit 46, either when the cuff pressure has dropped below a predetermined pressure or a predetermined time has elapsed after the beginning of the deflation portion of the cycle. The $P_D$ pulse is used in the measurement cycle control circuit to complete the measurement cycle by conditioning the dump valve 36 to open and turning off the recorder 38. The output which performs these functions is the PORD output of the measurement cycle control circuit 46.

The manual events, and the manual blood pressure measurement cycle, are each initiated by the manual event pulse generator 52, which may include the switch 44. If an automatic event preceded the manual event as indicated by the output AP from the measurement cycle control circuit 46 and if a measurement cycle is not ongoing or in progress at the time of the manual event pulse from the generator 52, a manual event pulse is inputted to the measurement cycle control circuit to initiate a manual measurement cycle.

In the event that the time base during which the auscultatory sounds are recorded is not linear, the exact pressure corresponding to the systolic and diastolic pressures of the subject cannot be accurately determined. The recorded signals are used to indicate the blood pressure. An operator examines an oscillogram obtained by playing back the recorded signals. Inasmuch as steps or pulses corresponding to the high and low reference pressures $P_H$ and $P_L$ are also recorded, the auscultatory sounds, if they occur on a linear time base corresponding to the cuff pressure, will indicate the systolic and diastolic pressure to a high degree of accuracy. Various attempts which have been made to linearize the change in cuff pressure have involved complex fluidic control (see U.S. Pat. No. 4,167,181 issued Sept. 11, 1979) or have relied upon the Korotkoff sounds themselves to control the cuff pressure (see U.S. Pat. No. 4,116,230 issued Sept. 26, 1978). The pressure ramp linearization circuits 56 which are provided in accordance with this invention provide a linear change in pressure which occurs during the deflation portion of the cycle in this preferred emodiment and are compatible with portable, compact or miniaturized apparatus which is adapted to be worn or carried by the subject. It may be mentioned that all of the apparatus shown in FIG. 1 with the exception of the cuff 10 and the tubes 12 and 14 and of the microphone 16 are adapted to be contained in a small package which may be carried or worn by the subject.

The linearization circuits 56 include a ramp generator 58 which generates a linear reference ramp upon occurrence of the ramp down control level, RD, from the measurement cycle control circuit 46. If the pressure in the cuff deviates from a linearly decreasing pressure as represented by the ramp from the ramp generator 58, the width of the pulses from the variable width pulse generator 62 changes. Accordingly, the modulator valve is opened or closed for varying intervals of time during the deflation cycle to insure that the pressure decreases linearly during the deflation cycle. The sawtooth waves from the sawtooth oscillator have a period which is much smaller than the duration of the ramp such that many sawtooth waves occur during the ramp. These sawtooth waves are converted into pulses of varying widths depending upon the deviation of the pulse pressure from the desired linear ramp. If the cuff pressure goes down faster than the ramp, the positive pulses become wider and the modulator valve stays closed for a longer period of time during each pulse period. Conversely, if the cuff pressure decreases less rapidly than the ramp, the positive pulses to the modulating valve decrease in width. Accordingly, correspondence of the cuff pressure to the linear reference ramp is maintained throughout the deflation portion of the cycle.

In order to close the modulating valve when the pump is operating and to insure that the modulating valve modulates the cuff pressure only during the deflation portion of the cycle to commands from the measurement cycle control circuit 46, RD and PO are applied to the modulator valve control circuit 64. Accordingly, during the inflation portion of the cycle, and when the ramp down condition is not called for by the measurement cycle control circuit 46, the output to the modulator valve 34 is of such polarity as to maintain that valve closed. The modulator valve therefore does not interfere with the inflation of the cuff, nor is it active otherwise except to control the linearization of the change in pressure during the deflation cycle.

Figure 2:
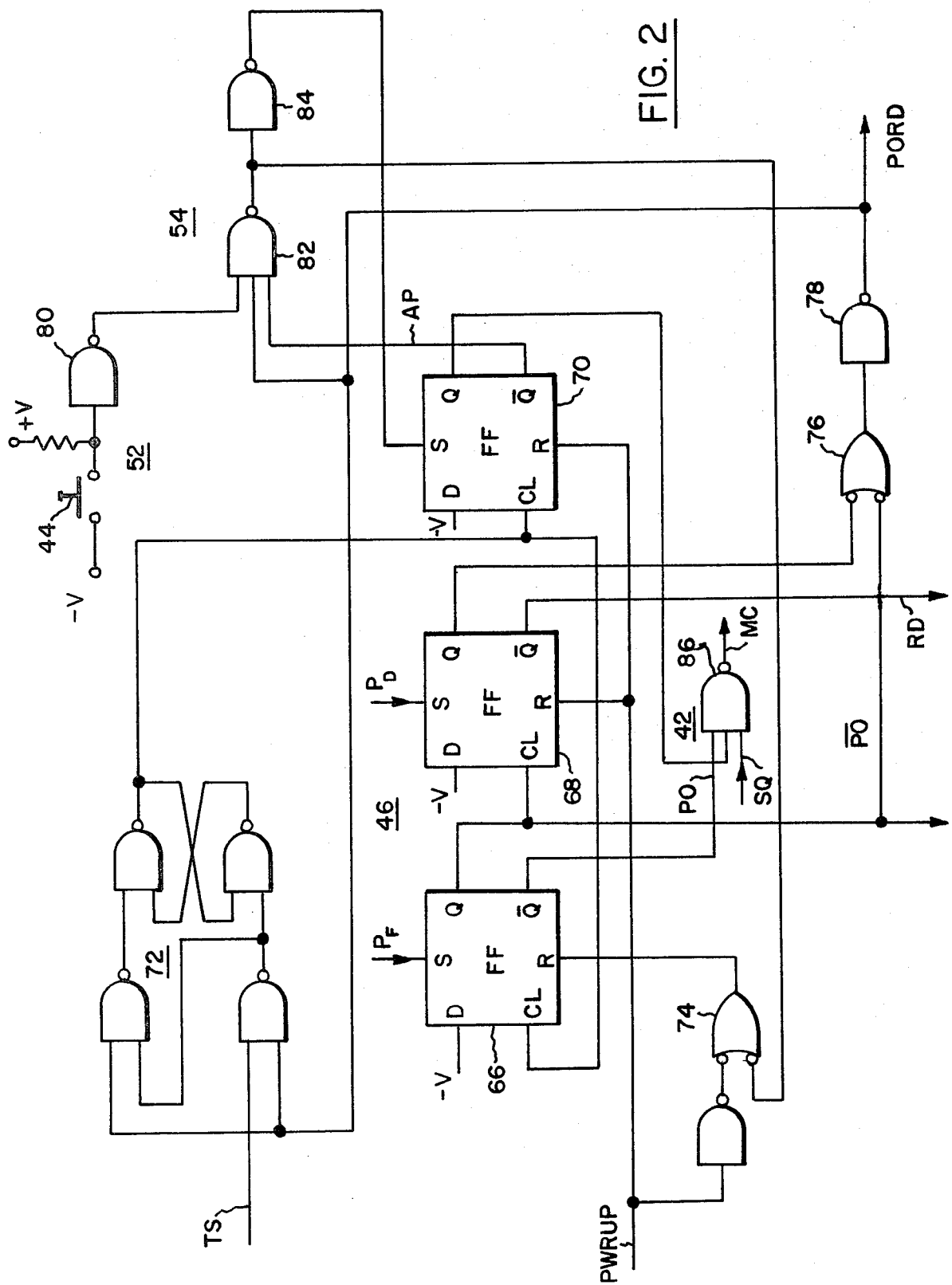
FIG. 2 is a diagram showing the measurement cycle control circuits of the apparatus illustrated in FIG. 1 in greater detail.

Referring to FIG. 2, there is shown the measurement cycle control circuit 46. This circuit includes three D-type flip flops 66, 68 and 70. The automatic event command signals TS are applied to the clock input of the first and third of the flip flops 66 and 70 by means of a gated latch circuit 72. This circuit remembers that an event is in progress and is not responsive to any other pulses until the end of a measurement cycle when the trailing edge of the PORD control level is applied thereto. The leading edge of the output of the latch portion of the gated latch circuit 72 clocks the first and third flip flops 66 and 70. These flip flops are initially, upon power up of the apparatus, reset through the gate 74. This gate 74 is a NOR gate as indicated by the standard symbol therefor used in the drawing. The reset condition of the first flip flop 66 produces the PO command. In other words, upon power up, the first measurement cycle is initiated. The first flip flop 66 is similarly set in the same state as it is in when reset due to the connection of the negative voltage to the D input of the flip flop. Accordingly, a TS pulse from the latch portion of the gated latch 72 also results in the PO output which causes the motor 30 to start the pump and inflate the cuff. The inflation continues until the PF pulse sets the flip flop to its alternate state. The PO level changes and the pump is shut off. The diaphragm of the pump, keeps the manifold closed and sealed through the pump 28 when the pump is not pumping. The change in state of the first or pump control flip flop 66 clocks the ramp on or second flip flop 68 which produces the RD level. This level is applied to the ramp generator 58 and initiates the deflation cycle by operating the pressure ramp linearization circuit 56 to in turn operate the modulator valve 34 through its control circuit 64. The modulator valve operation and the ramp continues until the $P_D$ pulse sets the ramp control flip flop 68 to its opposite state, a NOR gate 76 and an inverter gate 78 provides a PORD level of proper polarity during the measurement cycle, i.e., when the pump is on or when the ramp is on and the cuff is being deflated. During the deflation cycle, the auscultatory sounds are sensed and recorded by the recorder 38, as on a magnetic tape. The manual inflation is controlled by the third flip flop 70. This flip flop 70 is clocked through the latch gate 72 when an automatic cycle is initiated by the TS pulse, but only if a measurement cycle is not in progress as indicated by the PORD level, and then a manual cycle is allowed.

The manual cycle is initiated by the subject by pressing the switch 44. The switch 44 generates a pulse which is converted into proper polarity by the gate 80. This is a NAND gate, as indicated by the use of the standard symbol therefor shown on the drawing. The switch 44 and its associated circuits together with the gate 80 provide the manual event pulse generator 52. The manual event control circuit 54 is provided by the NAND gate 82 to which the PORD output and an output AP from the third flip flop 70 are applied together with the manual event pulse. The AP output enables the gate 82 and the PORD output also enables the gate 82, only when both are present in the proper polarity, in this case high. This occurs only if a measurement cycle is not in progress and the manual control flip flop 70 has been reset or clocked so as to indicate that a preceding automatic cycle has occurred. Then the pulse generated upon operation of the manual switch 44 is transmitted through the gate 82 and the gate 74 to reset the pump on flip flop 66. This generates the PO output to cause the pump to operate and begin a manually activated blood pressure measurement cycle. Another gate 84 provides the manual cycle initiating pulse in proper polarity to set the third flip flop 70. The AP input to the gate 82 is then of a level which inhibits the gate. Accordingly, a second manual cycle is not possible until after another automatic cycle has occurred.

The AM output from the third flip flop 70 is applied to a gate 86 which functions as the manual code circuit 42 (see FIG. 1). The SQ signal is passed by the gate 86 only if the pump is on and a manual cycle has been commanded as indicted by the set condition of the third flip flop 70. The manual code signal $M_C$, which is the SQ signal (for example 4.8 Hz square waves) is applied to the input amplifier of the recorder 38 as explained above.

Figure 3:
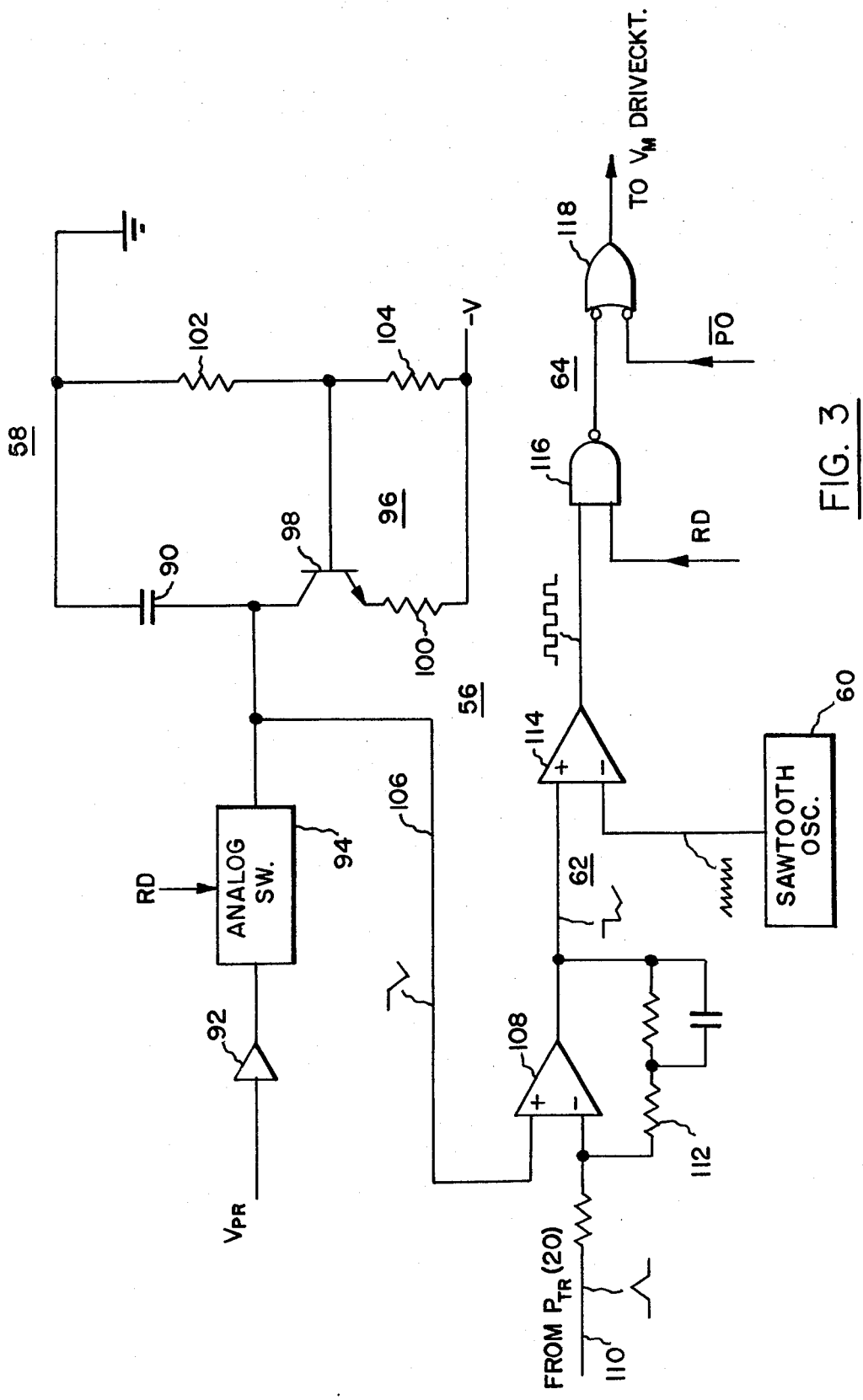
FIG. 3 is a diagram showing the pressure ramp linearization and modulator valve control circuits of the apparatus shown in FIG. 1 in greater detail.

The pressure ramp linearization circuit 56 is shown in FIG. 3. The ramp generator 58 uses a capacitor 90 which is charged to a reference voltage corresponding to the highest pressure to which the pump is allowed to inflate the cuff. This may be the same pressure as is reached when the signal $P_F$ is generated (e.g., 240 or 200 mm of Hg). The reference voltage $V_{PR}$ is applied to a buffer amplifier 92 and an analog switch 94 to the capacitor 90. The analog switch 94 is controlled by the RD level, which is high except during the deflation cycle when the ramp down control flip flop 68 is either clocked or reset (see FIG. 2). When RD goes low, the analog switch 94 opens and the capacitor 90 discharges through a constant current source 96 made up of a transistor 98, the bias of which is set by a regulated voltage source indicated as $-V$ through resistors 100, 102 and 104. Accordingly, a negative going ramp, as shown by the wave form adjacent to the line 106, is applied to a first difference amplifier 108, which serves as a comparator in the variable width pulse generator 62.

The pressure transducer signal from the pressure transducer 20 is applied to one input of the amplifier 108 and is an increasing ramp during the inflation portion of the cycle followed by a decreasing ramp during the deflation portion of the cycle. This signal from the transducer 20 is shown adjacent to the line 110 at the input of the difference amplifier 108. The difference amplifier is provided with a feed back circuit 112 which imparts some gain thereto. The output as a result of the comparison of the ramp with the pressure transducer signal appears at the output of the amplifier 108. At the beginning of the ramp, the output drops as the pressure transducer signal and the ramp become of approximately equal amplitude. Then, as the pressure transducer signal deviates from the ramp, the level at the output of the difference amplifier 108 changes. This changing level is compared with the high frequency sawtooth wave from the oscillator 60 in a second difference amplifier 114. The output as a result of this comparison is the width modulated pulses. These pulses are applied to NAND and NOR gates 116 and 118 which constitute the modulator valve control circuit 64. The RD and PO outputs applied to these gates insure that the modulator valve 34 is closed during pump on, open during system off, and modulating during the ramp down of deflation portion of the cycle.

The output from the gate 118 is applied to a drive circuit which drives the solenoid of the modulator valve 34 to open and close the valve during different periods of time depending upon deviation in the cuff pressure from the ramp, as explained above. Accordingly, a linear change in pressure is produced which provides a linear, calibrated time base during which the auscultatory sounds are sensed. The recording of the auscultatory sounds, and the $P_H$ and the $P_L$ signals permits the determination of the systolic and diastolic blood pressure of the subject during each measurement cycle with a high degree of accuracy. The recorder 38 may be adapted to record FM signals and operate at such speed as to record the entire spectrum of the sounds with high fidelity. The auscultatory sounds are therefore faithfully recorded and played back so that they may be displayed on an oscilloscope (CRT) display or as an auscillogram with a high degree of precision. The oscilloscope (CRT) display may be computerized such that information as to the blood pressure at the location of a particular auscultatory sound is generated in the form of computer data and stored in computer memory, for example on a disc. Information as to the time of day is provided from the automatic cycles which occur at regular, preset intervals, e.g. every hour, half-hour, etc. The auscultatory sound locations which represent the blood pressure level provide a printout, of the subject's blood pressure, during the entire long term, and for each of the recordings. The computer may also read the manual code and identify a measurement as a result of a manual event.

From the foregoing description it will be apparent that there has been provided improved blood pressure measurement apparatus especially suitable for long term recording of blood pressure measurement. Variations and modifications of the herein described apparatus, within the scope of the invention, will undoubtedly suggest themselves skilled in the art. Accordingly, the foregoing description should be taken as illustrative and not in a limiting sense.

We claim:

1. Blood pressure measurement apparatus using an inflatable cuff which constricts an appendage of a subject whose blood pressure is to be measured, said apparatus comprising means for changing the pressure in the cuff, means for sensing the auscultatory sounds from the appendage while the pressure in the cuff is changing, means for producing a signal having an amplitude which corresponds with the pressure in the cuff, valve means for modulating the pressure in the cuff as the pressure changes during the sensing of said auscultatory sounds, and means for controlling said valve means to linearize the change in pressure in said cuff which comprises means for generating a reference, linear ramp signal, which starts prior to the sensing of said auscultatory sounds, means for comparing said reference signal with said pressure signal to produce a first output corresponding to the difference in amplitude therebetween, means for generating a train of repetitive triangular waves each having a period much less than the duration of said ramp signal, means for comparing such repetitive triangular waves with said first output to produce a train of pulses, the durations of the pulses varying in accordance with the magnitude and sense of deviation of said pressure signal from said linear ramp signal, and means for applying said variable duration pulses to said valve means for opening and closing said valve means in accordance with the duration of the pulses in said pulse train such that the pressure in said cuff changes linearly in amplitude, correspondingly with said ramp signal.

2. The invention as set forth in claim 1 further comprising blood pressure measurement cycle control means for initiating and controlling cycles during each of which said auscultatory sounds are sensed, means in said cycle control means for operating said ramp generating means to start said ramp signal, said means for changing the pressure in said cuff including a pump, and means in said cycle control means for operating said pump.

3. The invention as set forth in claim 2 further comprising means responsive to said pressure signal for detecting when said cuff pressure has reached a first predetermined high pressure for operating said pump operating means and said cycle control means to stop said pump from increasing the pressure in said cuff.

4. The invention as set forth in claim 3 further comprising means in said cycle control means responsive to the initiation thereby of a measurement cycle for operating said pump operating means to stop said pump from increasing the pressure in said cuff a predetermined period of time after the initiation of each of said cycles.

5. The invention as set forth in claim 2 further comprising means included in said cycle control means for inhibiting the application of said pulses which vary in duration to said valve means except when said ramp signal is being generated.

6. The invention as set forth in claim 2 further comprising a second valve adapted to be in communication with said cuff, and means in said cycle control means for opening said second valve to release any pressure in said cuff except when any of said pump operating means is operating to increase the pressure in said cuff and said ramp signal generating means is operative to generate said ramp signal.

7. The invention as set forth in claim 1 further comprising means for detecting the pressure in said cuff and providing at least a first signal when said pressure is a certain relatively high pressure and a second signal when said pressure is a certain relatively low pressure, recorder means responsive to said sensing means for recording signals corresponding to said auscultatory sounds, and means for recording said first and second signals with said auscultatory sound signals to provide a scale of pressure which corresponds in linearity to said ramp signal for indicating the pressures corresponding to said auscultatory sounds.

8. The invention as set forth in claim 7 further comprising blood pressure measurement cycle control means for initiating cycles during each of which said auscultatory sounds are sensed, said means for changing the pressure in said cuff being a pump, means in said cycle control means for starting said pump and said recorder means, means in said pressure detecting means for providing an output when said cuff pressure reaches a certain pressure which is sufficiently above the higher systolic pressure of said subject to enable an auscultatory sound corresponding to said systolic pressure to be sensed, means in said cycle control means responsive to said above-systolic pressure output from said pressure detecting means for stopping said pump without stopping said recorder means and initiating said ramp signal whereby said modulating valve means is operated by said modulating valve control means to provide a linearly decreasing pressure in said cuff while said auscultatory sounds are recorded.

9. The invention as set forth in claim 8 further comprising means manually operable by the subject for providing first output commands to initiate a measurement cycle, means for providing successive second output commands automatically at selected intervals of time, said second output commands also to initiate automatic measurement cycles, means in said measurement cycle control means responsive to said first and second output commands for starting said pump and said recording means and controlling a measurement cycle.

10. The invention as set forth in claim 9 further comprising means responsive to each of said first output commands for generating a signal indicative of said manual measurement cycle and applying said manual measurement cycle signal to said recording means for recording said signal to distinguish recordings of manual and automatic measurement cycles.

11. The invention as set forth in claim 9 further comprising means included in said measurement cycle control means for inhibiting the initiation of a manual measurement cycle in response to said first output commands if they occur with greater than a certain frequency.

12. The invention as set forth in claim 11 wherein said means in said measurement cycle control means for inhibiting the initiation of said manual measurement cycle comprises means operated by said automatic second output commands for inhibiting said manual first output commands from initiating a measurement cycle unless one of said automatic second output commands has preceded said one of said first output commands and initiated an automatic cycle immediately before the initiation of a manual cycle.

13. The invention as set forth in claim 12 wherein said measurement cycle control means further comprises means for inhibiting the initiation of a measurement cycle in response to said first output commands when a prior measurement cycle is in progress.

14. The invention as set forth in claim 1 wherein said ramp generating means comprises a capacitor, means for charging said capacitor to a voltage corresponding in amplitude to a pressure in said cuff above the systolic pressure of said subject, a current source circuit connected to said capacitor, means operative for switching current from said capacitor to said current source to generate the linear reference ramp signal, wherein said means for comparing said ramp signal with said pressure signal comprises a first difference amplifier which produces a first output, and wherein said means for comparing said triangular waves with said first output comprises a second difference amplifier which produces said variable duration pulses for opening and closing said modulator valve means to produce linearly decreasing pressure in said cuff while said auscultatory sounds are sensed.

15. The invention as set forth in claim 14 wherein said triangular wave generating means is a sawtooth signal oscillator.

16. Longterm, portable blood pressure monitoring apparatus, for use with an inflatable cuff which is applied to the appendage of the subject whose blood pressure is to be measured, said apparatus comprising means including a pump for inflating said cuff, transducer means for sensing the pressure in said cuff, means for detecting auscultatory sounds from the appendage to which said cuff is applied, means for recording said sounds, means for producing successive first commands at predetermined periods of time for initiating automatically blood pressure measurement cycles at predetermined intervals, means operable manually by the subject for producing upon each operation a second command for initiating manually a blood pressure measurement cycle, means for controlling said blood pressure measurement cycle by operating said pump until the pressure in said cuff reaches a predetermined pressure above the systolic pressure of the subject, said pump being started at the beginning of said cycle and said cuff being deflated below the diastolic pressure of the subject at the end of said cycle, and for operating said recording means during said cycle, means in said cycle control means for producing a measurement cycle upon occurrence of each of said first commands, and means in said cycle control means for producing a measurement cycle upon occurrence of said second command which do not recur with more than a certain frequency.

17. The invention as set forth in claim 16 wherein said means for producing a measurement cycle in response to said second command include means responsive to said first commands for inhibiting said second command from producing a measurement cycle unless a first command occurs between successive second commands.

18. The invention as set forth in claim 17 wherein valve means are provided for controlling the pressure in said pump and said measurement cycle control means comprises three flip flops, a first of said flip flops being coupled to said pump, a second of said flip flops being coupled to control said valve means, and a third of said flip flops being included in said means for inhibiting the production of said manual cycle upon occurrence of said second command, said means for inhibiting said production of manual measurement cycles including a gate circuit, means responsive to said first commands for conditioning said first and third flip flops into one of their two alternate states which causes the operation of said pump and enables said gate circuit, means responsive to the pressure in said cuff reaching said predetermined pressure for conditioning said first flip flop into the other of its alternate states to stop said pump, means coupling said first flip flop to said second flip flop to condition said second flip flop into the one of its alternate states which causes operation of said valve means, means for conditioning said second flip flop into the other of its alternate states when the pressure in said cuff reaches said pressure below diastolic pressure of the subject, and means connecting said first and second flip flops to said gate circuit for inhibiting said gate circuit when said first flip flop or said second flip flop is in said one of said alternate states thereof, and said gate circuit being connected to said first flip flop for conditioning said first flip flop into said one state thereof upon occurrence of said second command when said gate circuit is enabled.

19. The invention as set forth in claim 18 further comprising gated latch means for conditioning said first and third flip flops into said one of said alternate states thereof upon occurrence of said first command.

20. The invention as set forth in claim 17 further comprising means for generating a manual control signal and means controlled by said manual control signal generating means in said cycle control means for producing a measurement cycle for applying a marker signal to said recording means only upon occurrence of said manual control signal to distinguish automatically and manually initiated blood pressure measurement cycles from each other on the recording produced by said recording means.

21. The invention as set forth in claim 16 wherein said means for producing a measurement cycle in response to said second command includes means operative when a measurement cycle is in progress for preventing said second command from producing a measurement cycle.

* * * * *